United States Patent
Carling et al.

(10) Patent No.: US 6,699,859 B1
(45) Date of Patent: Mar. 2, 2004

(54) TRIAZOLO-PYRIDAZINE DERIVATIVES AS LIGANDS FOR GABA RECEPTORS

(75) Inventors: William Robert Carling, Bishops Stortford (GB); Andrew Mitchinson, Sawbridgeworth (GB); Leslie Joseph Street, Little Hallingbury (GB)

(73) Assignee: Merck Sharp & Dohme Ltd., Hoddesdon (GB)

( * ) Notice: Subject to any disclaimer, the term of this patent is extended or adjusted under 35 U.S.C. 154(b) by 0 days.

(21) Appl. No.: 09/582,445

(22) PCT Filed: Jan. 13, 1999

(86) PCT No.: PCT/GB99/00106

§ 371 (c)(1), (2), (4) Date: Jun. 26, 2000

(87) PCT Pub. No.: WO99/37646

PCT Pub. Date: Jul. 29, 1999

(30) Foreign Application Priority Data

Jan. 21, 1998 (GB) .............................................. 9801202

(51) Int. Cl.$^7$ ...................... A61P 25/08; A60K 31/5025; C07D 401/04; C07D 413/04; C07D 417/04
(52) U.S. Cl. ................................ 514/228.5; 514/233.2; 514/252; 514/253; 544/61; 544/118; 544/236
(58) Field of Search ................................. 544/236, 118, 544/61; 514/233.2, 228.5, 253, 252

(56) References Cited

U.S. PATENT DOCUMENTS

| | | | |
|---|---|---|---|
| 4,112,095 A | 9/1978 | Allen, Jr. et al. | 424/250 |
| 4,117,130 A | 9/1978 | Allen, Jr. et al. | 424/250 |
| 4,230,705 A | 10/1980 | Allen, Jr. et al. | 424/250 |
| 4,260,755 A | 4/1981 | Moran et al. | 544/236 |
| 4,260,756 A | 4/1981 | Moran et al. | 544/236 |
| 4,654,343 A | 3/1987 | Albright et al. | 514/248 |
| 6,001,830 A * | 12/1999 | Lee et al. | 514/248 |
| 6,255,305 B1 * | 7/2001 | Broughton et al. | 514/248 |

FOREIGN PATENT DOCUMENTS

| | | |
|---|---|---|
| DE | 27 41 763 | 9/1977 |
| EP | 0 085 840 | 8/1983 |
| EP | 0 134 946 | 3/1985 |
| GB | 1 589 237 | 5/1991 |
| WO | WO 98/04559 | 2/1998 |

OTHER PUBLICATIONS

Bayley, et al., J. Psychopharmacol., 10:206–213 (1996).
Bristow, et al., J. Pharmacol. Exp. Ther., 279: 492–501 (1996).
Dawson, et al., Psychoparmacology, 121: 109–117 (1995).
Wafford, et al., Mol. Pharmacol., 50: 670–678 (1996).

* cited by examiner

Primary Examiner—Bruck Kifle
Assistant Examiner—U. Mallikarjuna Rao
(74) Attorney, Agent, or Firm—Shu Muk Lee; David L. Rose

(57) ABSTRACT

1,2,4-triazolo[4,3-b]pyridazine derivatives, possessing an optionally substituted cycloalkyl, phenyl or heteroaryl substituent at the 3-position, a substituted alkoxy moiety at the 6-position, an optionally substituted N-linked nitrogen-containing aliphatic ring at the 7-position, and a chloro at the 8-position are selective ligands for GABAZ$_A$ receptors, in particular having high affinity for the α2 and/or α3 subunit thereof, are useful in the treatment of anxiety and convulsions.

8 Claims, No Drawings

TRIAZOLO-PYRIDAZINE DERIVATIVES AS LIGANDS FOR GABA RECEPTORS

This is an application under 35 U.S.C. 371 of PCT/GB99/00106 and claims priority from Great Britain Application No. 9801202.4, filed Jan. 21, 1998.

The present invention relates to a class of substituted triazolo-pyridazine derivatives and to their use in therapy. More particularly, this invention is concerned with substituted 1,2,4-triazolo[4,3-b]pyridazine derivatives which are ligands for $GABA_A$ receptors and are therefore useful in the therapy of deleterious mental states.

Receptors for the major inhibitory neurotransmitter, gamma-aminobutyric acid (GABA), are divided into two main classes: (1) $GABA_A$ receptors, which are members of the ligand-gated ion channel superfamily; and (2) $GABA_B$ receptors, which may be members of the G-protein linked receptor superfamily. Since the first cDNAs encoding individual $GABA_A$ receptor subunits were cloned the number of known members of the mammalian family has grown to include at least six $\alpha$ subunits, four $\beta$ subunits, three $\gamma$ subunits, one $\delta$ subunit, one $\epsilon$ subunit and two $\rho$ subunits.

Although knowledge of the diversity of the $GABA_A$ receptor gene family represents a huge step forward in our understanding of this ligand-gated ion channel, insight into the extent of subtype diversity is still at an early stage. It has been indicated that an $\alpha$ subunit, a $\beta$ subunit and a $\gamma$ subunit constitute the minimum requirement for forming a fully functional $GABA_A$ receptor expressed by transiently transfecting cDNAs into cells. As indicated above, $\delta$, $\epsilon$ and $\rho$ subunits also exist, but are present only to a minor extent in $GABA_A$ receptor populations.

Studies of receptor size and visualisation by electron microscopy conclude that, like other members of the ligand-gated ion channel family, the native $GABA_A$ receptor exists in pentameric form. The selection of at least one $\alpha$, and $\beta$ and one $\gamma$ subunit from a repertoire of seventeen allows for the possible existence of more than 10,000 pentameric subunit combinations. Moreover, this calculation overlooks the additional permutations that would be possible if the arrangement of subunits around the ion channel had no constraints (i.e. there could be 120 possible variants for a receptor composed of five different subunits).

Receptor subtype assemblies which do exist include, amongst many others, $\alpha1\beta2\gamma2$, $\alpha2\beta2/3\gamma2$, $\alpha3\beta\gamma2/3$, $\alpha2\beta\gamma1$, $\alpha5\beta3\gamma2/3$, $\alpha6\beta\gamma2$, $\alpha6\beta\delta$ and $\alpha4\beta\delta$. Subtype assemblies containing an $\alpha1$ subunit are present in most areas of the brain and are thought to account for over 40% of $GABA_A$ receptors in the rat. Subtype assemblies containing $\alpha2$ and $\alpha3$ subunits respectively are thought to account for about 25% and 17% of $GABA_A$ receptors in the rat. Subtype assemblies containing an $\alpha5$ subunit are expressed predominantly in the hippocampus and cortex and are thought to represent about 4% of $GABA_A$ receptors in the rat.

A characteristic property of all known $GABA_A$ receptors is the presence of a number of modulatory sites, one of which is the benzodiazepine (BZ) binding site. The BZ binding site is the most explored of the $GABA_A$ receptor modulatory sites, and is the site through which anxiolytic drugs such as diazepam and temazepam exert their effect. Before the cloning of the $GABA_A$ receptor gene family, the benzodiazepine binding site was historically subdivided into two subtypes, BZ1 and BZ2, on the basis of radioligand binding studies. The BZ1 subtype has been shown to be pharmacologically equivalent to a $GABA_A$ receptor comprising the $\alpha1$ subunit in combination with a $\beta$ subunit and $\gamma2$. This is the most abundant $GABA_A$ receptor subtype, and is believed to represent almost half of all $GABA_A$ receptors in the brain.

Two other major populations are the $\alpha2\beta\gamma2$ and $\alpha3\beta\gamma2/3$ subtypes. Together these constitute approximately a further 35% of the total $GABA_A$ receptor repertoire. Pharmacologically this combination appears to be equivalent to the BZ2 subtype as defined previously by radioligand binding, although the BZ2 subtype may also include certain $\alpha5$-containing subtype assemblies. The physiological role of these subtypes has hitherto been unclear because no sufficiently selective agonists or antagonists were known.

It is now believed that agents acting as BZ agonists at $\alpha1\beta\gamma2$, $\alpha2\beta\gamma2$ or $\alpha3\beta\gamma2$ subunits will possess desirable anxiolytic properties. Compounds which are modulators of the benzodiazepine binding site of the $GABA_A$ receptor by acting as BZ agonists are referred to hereinafter as "$GABA_A$ receptor agonists". The $\alpha1$-selective $GABA_A$ receptor agonists alpidem and zolpidem are clinically prescribed as hypnotic agents, suggesting that at least some of the sedation associated with known anxiolytic drugs which act at the BZ1 binding site is mediated through $GABA_A$ receptors containing the $\alpha1$ subunit. Accordingly, it is considered that $GABA_A$ receptor agonists which interact more favourably with the $\alpha2$ and/or $\alpha3$ subunit than with $\alpha1$ will be effective in the treatment of anxiety with a reduced propensity to cause sedation. Also, agents which are antagonists or inverse agonists at $\alpha1$ might be employed to reverse sedation or hypnosis caused by $\alpha1$ agonists.

The compounds of the present invention, being selective ligands for $GABA_A$ receptors, are therefore of use in the treatment and/or prevention of a variety of disorders of the central nervous system. Such disorders include anxiety disorders, such as panic disorder with or without agoraphobia, agoraphobia without history of panic disorder, animal and other phobias including social phobias, obsessive-compulsive disorder, stress disorders including post-traumatic and acute stress disorder, and generalized or substance-induced anxiety disorder; neuroses; convulsions; migraine; depressive or bipolar disorders, for example single-episode or recurrent major depressive disorder, dysthymic disorder, bipolar I and bipolar II manic disorders, and cyclothymic disorder; psychotic disorders including schizophrenia; neurodegeneration arising from cerebral ischemia; attention deficit hyperactivity disorder; and disorders of circadian rhythm, e.g. in subjects suffering from the effects of jet lag or shift work.

Further disorders for which selective ligands for $GABA_A$ receptors may be of benefit include pain and nociception; emesis, including acute, delayed and anticipatory emesis, in particular emesis induced by chemotherapy or radiation, as well as post-operative nausea and vomiting; eating disorders including anorexia nervosa and bulimia nervosa; premenstrual syndrome; muscle spasm or spasticity, e.g. in paraplegic patients; and hearing loss. Selective ligands for $GABA_A$ receptors may also be effective as pre-medication prior to anaesthesia or minor procedures such as endoscopy, including gastric endoscopy.

In DE-A-2741763, and in U.S. Pat. Nos. 4,260,755, 4,260,756 and 4,654,343, are described various classes of 1,2,4-triazolo[4,3-b]pyridazine derivatives which are alleged to be useful as anxiolytic agents. The compounds described in DE-A-2741763 and in U.S. Pat. Nos. 4,260,755 and 4,654,343 possess a phenyl substituent at the 6-position of the triazolo-pyridazine ring system. The compounds described in U.S. Pat. No. 4,260,756, meanwhile, possess a heteroaryl moiety at the 6- or 8-position. In none of these publications, however, is there any disclosure or suggestion of 1,2,4-triazolo[4,3-b]pyridazine derivatives wherein the substituent at the 6-position is attached through a directly linked oxygen atom.

EP-A-0085840 and EP-A-0134946 describe related series of 1,2,4-triazolo[3,4-α]phthalazine derivatives which are stated to possess antianxiety activity. However, there is no disclosure nor any suggestion in either of these publications of replacing the benzo moiety of the triazolophthalazine ring system with any other functionality.

The present invention provides a class of triazolopyridazine derivatives which possess desirable binding properties at various GABA$_A$ receptor subtypes. The compounds in accordance with the present invention have good affinity as ligands for the α2 and/or α3 subunit of the human GABA$_A$ receptor. The compounds of this invention may interact more favourably with the α2 and/or α3 subunit than with the α1 subunit. Desirably, the compounds of the invention will exhibit functional selectivity in terms of a selective efficacy for the α2 and/or α3 subunit relative to the α1 subunit.

The compounds of the present invention are GABA$_A$ receptor subtype ligands having a binding affinity ($K_i$) for the α2 and/or α3 subunit, as measured in the assay described hereinbelow, of 100 nM or less, typically of 50 nM or less, and ideally of 10 nM or less. The compounds in accordance with this invention may possess at least a 2-fold, suitably at least a 5-fold, and advantageously at least a 10-fold, selective affinity for the α2 and/or α3 subunit relative to the α1 subunit. However, compounds which are not selective in terms of their binding affinity for the α2 and/or α3 subunit relative to the α1 subunit are also encompassed within the scope of the present invention; such compounds will desirably exhibit functional selectivity in terms of a selective efficacy for the α2 and/or α3 subunit relative to the α1 subunit.

The present invention provides a compound of formula I, or a salt or prodrug thereof:

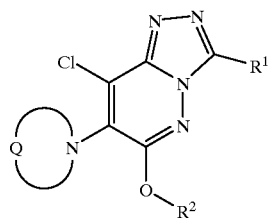

(I)

wherein

Q represents the residue of an optionally substituted azetidine, pyrrolidine, piperidine, morpholine or thiomorpholine ring;

$R^1$ represents $C_{3-7}$ cycloalkyl, phenyl, furyl, thienyl or pyridinyl, any of which groups may be optionally substituted; and $R^2$ represents cyano($C_{1-6}$)alkyl, hydroxy($C_{1-6}$)alkyl, $C_{3-7}$ cycloalkyl($C_{1-6}$)alkyl, propargyl, $C_{3-7}$ heterocycloalkylcarbonyl($C_{1-6}$)alkyl, aryl($C_{1-6}$)alkyl or heteroaryl ($C_{1-6}$)alkyl, any of which groups may be optionally substituted.

The groups $R^1$ and $R^2$, and the ring of which Q is the residue, may be unsubstituted, or substituted by one or more, suitably by one or two, substituents. In general, the groups $R^1$ and $R^2$, and the ring of which Q is the residue, will be unsubstituted or monosubstituted. Examples of optional substituents on the groups $R^1$ and $R^2$, and the ring of which Q is the residue, include $C_{1-6}$ alkyl, aryl($C_{1-6}$)alkyl, pyridyl ($C_{1-6}$)alkyl, halogen, halo($C_{1-6}$)alkyl, cyano, cyano($C_{1-6}$) alkyl, hydroxy, hydroxymethyl, $C_{1-6}$ alkoxy, $C_{3-7}$ cycloalkyl ($C_{1-6}$)alkoxy, $C_{3-7}$ cycloalkoxy, amino($C_{1-6}$)alkyl, di($C_{1-6}$) alkylamino($C_{1-6}$)alkyl, di($C_{1-6}$)alkylaminocarbonyl($C_{1-6}$) alkyl, N-($C_{1-6}$)alkylpiperidinyl, pyrrolidinyl($C_{1-6}$)alkyl, piperazinyl($C_{1-6}$)alkyl, morpholinyl($C_{1-6}$)alkyl, di($C_{1-6}$) alkylmorpholinyl($C_{1-6}$)alkyl and imidazolyl($C_{1-6}$)alkyl. Representative substituents include $C_{1-6}$ alkyl, aryl($C_{1-6}$) alkyl, halogen, cyano, hydroxy, hydroxymethyl, $C_{1-6}$ alkoxy and $C_{3-7}$ cycloalkyl($C_{1-6}$)alkoxy, especially $C_{1-6}$ alkyl or halogen.

As used herein, the expression "$C_{1-6}$ alkyl" includes methyl and ethyl groups, and straight-chained or branched propyl, butyl, pentyl and hexyl groups. Particular alkyl groups are methyl, ethyl, n-propyl, isopropyl, tert-butyl and 1,1-dimethylpropyl. Derived expressions such as "$C_{1-6}$alkoxy" are to be construed accordingly.

Typical $C_{3-7}$ cycloalkyl groups include cyclopropyl, cyclobutyl, cyclopentyl and cyclohexyl.

The expression "$C_{3-7}$ cycloalkyl($C_{1-6}$)alkyl" as used herein includes cyclopropylmethyl, cyclobutylmethyl, cyclopentylmethyl and cyclohexylmethyl.

Typical aryl groups include phenyl and naphthyl, preferably phenyl.

The expression "aryl($C_{1-6}$)alkyl" as used herein includes benzyl, phenylethyl, phenylpropyl and naphthylmethyl.

Suitable heterocycloalkyl groups include azetidinyl, pyrrolidinyl, piperidinyl, piperazinyl, morpholinyl and thiomorpholinyl groups.

Suitable heteroaryl groups include pyridinyl, quinolinyl, isoquinolinyl, pyridazinyl, pyrimidinyl, pyrazinyl, quinoxalinyl, furyl, benzofuryl, dibenzofuryl, thienyl, benzthienyl, pyrrolyl, indolyl, pyrazolyl, indazolyl, oxazolyl, isoxazolyl, thiazolyl, isothiazolyl, imidazolyl, benzimidazolyl, oxadiazolyl, thiadiazolyl, triazolyl and tetrazolyl groups.

The expression "heteroaryl($C_{1-6}$)alkyl" as used herein includes furylmethyl, furylethyl, thienylmethyl, thienylethyl, pyrazolylmethyl, oxazolylmethyl, oxazolylethyl, isoxazolylmethyl, thiazolylmethyl, thiazolylethyl, imidazolylmethyl, imidazolylethyl, benzimidazolylmethyl, oxadiazolylmethyl, oxadiazolylethyl, thiadiazolylmethyl, thiadiazolylethyl, triazolylmethyl, triazolylethyl, tetrazolylmethyl, tetrazolylethyl, pyridinylmethyl, pyridinylethyl, pyridazinylmethyl, pyrimidinylmethyl, pyrazinylmethyl, quinolinylmethyl, isoquinolinylmethyl and quinoxalinylmethyl.

The term "halogen" as used herein includes fluorine, chlorine, bromine and iodine, especially fluorine or chlorine.

For use in medicine, the salts of the compounds of formula I will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The present invention includes within its scope prodrugs of the compounds of formula I above. In general, such prodrugs will be functional derivatives of the compounds of formula I which are readily convertible in vivo into the required compound of formula I. Conventional procedures for the selection and preparation of suitable prodrug derivatives are described, for example, in *Design of Prodrugs*, ed. H. Bundgaard, Elsevier, 1985.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof in any proportion are encompassed within the scope of the present invention.

The moiety Q suitably represents the residue of an optionally substituted pyrrolidine or morpholine ring. In a typical embodiment, the moiety Q represents the residue of a pyrrolidin-1-yl or morpholin-4-yl group, either unsubstituted or substituted by $C_{1-6}$ alkyl, especially methyl. Favourably, Q represents the residue of an unsubstituted pyrrolidin-1-yl or morpholin-4-yl moiety.

Examples of typical optional substituents on the group $R^1$ include methyl, fluoro and methoxy.

Representative values of $R^1$ include cyclopropyl, phenyl, methylphenyl, fluorophenyl, difluorophenyl, methoxyphenyl, furyl, thienyl, methyl-thienyl and pyridinyl. Suitably, $R^1$ may represent unsubstituted, monosubstituted or disubstituted phenyl. Particular values of $R^1$ include phenyl and thienyl.

Suitable values for the substituent $R^2$ in the compounds according to the invention include cyanomethyl, hydroxybutyl, cyclohexylmethyl, propargyl, pyrrolidinylcarbonylmethyl, benzyl, pyrazolylmethyl, isoxazolylmethyl, thiazolylmethyl, thiazolylethyl, imidazolylmethyl, benzimidazolylmethyl, oxadiazolylmethyl, triazolylmethyl, tetrazolylmethyl, pyridinylmethyl, pyridazinylmethyl, pyrimidinylmethyl, pyrazinylmethyl, quinolinylmethyl, isoquinolinylmethyl and quinoxalinylmethyl, any of which groups may be optionally substituted by one or more substituents. A typical value of $R^2$ is optionally substituted triazolylmethyl.

Examples of suitable optional substituents on the group $R^2$ include $C_{1-6}$ alkyl, aryl($C_{1-6}$)alkyl, pyridyl($C_{1-6}$)alkyl, halogen, halo($C_{1-6}$)alkyl, cyano, cyano($C_{1-6}$)alkyl, hydroxymethyl, $C_{1-6}$ alkoxy, $C_{3-7}$ cycloalkyl($C_{1-6}$)alkoxy, amino($C_{1-6}$)alkyl, di($C_{1-6}$)alkylamino($C_{1-6}$)alkyl, di($C_{1-6}$) alkylaminocarbonyl($C_{1-6}$)alkyl, N-($C_{1-6}$)alkylpiperidinyl, pyrrolidinyl($C_{1-6}$)alkyl, ($C_{1-6}$)alkyl, morpholinyl($C_{1-6}$)alkyl and di($C_{1-6}$)alkylmorpholinyl($C_{1-6}$)alkyl.

Specific illustrations of particular substituents on the group $R^2$ include methyl, ethyl, n-propyl, benzyl, pyridinylmethyl, chloro, chloromethyl, cyano, cyanomethyl, hydroxymethyl, ethoxy, cyclopropylmethoxy, dimethylaminomethyl, aminoethyl, dimethylaminoethyl, dimethylaminocarbonylmethyl, N-methylpiperidinyl, pyrrolidinylethyl, piperazinylethyl, morpholinylmethyl and dimethylmorpholinylmethyl, especially methyl.

Representative values of $R^2$ include cyanomethyl, hydroxybutyl, hydroxymethyl-cyclohexylmethyl, propargyl, dimethylaminomethyl-propargyl, dimethylmorpholinylmethyl-propargyl, pyrrolidinylcarbonylmethyl, cyanobenzyl, hydroxymethyl-benzyl, pyrazolylmethyl, dimethyl-pyrazolylmethyl, methyl-isoxazolylmethyl, thiazolylmethyl, methyl-thiazolylmethyl, ethyl-thiazolylmethyl, methyl-thiazolylethyl, imidazolylmethyl, methyl-imidazolylmethyl, ethyl-imidazolylmethyl, benzyl-imidazolylmethyl, benzimidazolylmethyl, methyl-oxadiazolylmethyl, triazolylmethyl, methyl-triazolylmethyl, propyl-triazolylmethyl, benzyl-triazolylmethyl, pyridinylmethyl-triazolylmethyl, cyanomethyl-triazolylmethyl, dimethylaminomethyl-triazolylmethyl, aminoethyl-triazolylmethyl, dimethylaminoethyl-triazolylmethyl, dimethylaminocarbonylmethyl-triazolylmethyl, N-methylpiperidinyl-triazolylmethyl, pyrrolidinylethyl-triazolylmethyl, piperazinylethyl-triazolylmethyl, morpholinylethyl-triazolylmethyl, methyl-tetrazolylmethyl, pyridinylmethyl, methyl-pyridinylmethyl, dimethyl-pyridinylmethyl, ethoxy-pyridinylmethyl, cyclopropylmethoxy-pyridinylmethyl, pyridazinylmethyl, chloro-pyridazinylmethyl, pyrimidinylmethyl, pyrazinylmethyl, quinolinylmethyl, isoquinolinylmethyl and quinoxalinylmethyl.

A favoured value of $R^2$ is methyl-triazolylmethyl.

A particular sub-class of compounds according to the invention is represented by the compounds of formula IIA, and salts and prodrugs thereof:

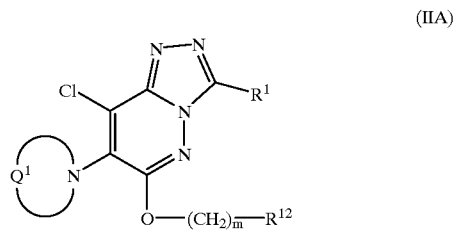

(IIA)

wherein $R^1$ is as defined with reference to formula I above;

m is 1 or 2, preferably 1;

$Q^1$ represents the residue of a pyrrolidine or morpholine ring; and $R^{12}$ represents aryl or heteroaryl, either of which groups may be optionally substituted.

Suitable values for $R^{12}$ include phenyl, pyrazolyl, isoxazolyl, thiazolyl, imidazolyl, benzimidazolyl, oxadiazolyl, triazolyl, tetrazolyl, pyridinyl, pyridazinyl, pyrimidinyl, pyrazinyl, quinolinyl, isoquinolinyl and quinoxalinyl, any of which groups may be optionally substituted.

Suitably, $R^{12}$ represents optionally substituted triazolyl.

Examples of typical substituents on the group $R^{12}$ include $C_{1-6}$ alkyl, aryl($C_{1-6}$)alkyl, pyridyl($C_{1-6}$)alkyl, halogen, cyano, cyano($C_{1-6}$)alkyl, hydroxymethyl, $C_{1-6}$ alkoxy, $C_{3-7}$ cycloalkyl($C_{1-6}$)alkoxy, di($C_{1-6}$)alkylamino($C_{1-6}$)alkyl, amino($C_{1-6}$)alkyl, di($C_{1-6}$) alkylaminocarbonyl($C_{1-6}$)alkyl, N-($C_{1-6}$) alkypiperidinyl, pyrrolidinyl($C_{1-6}$)alkyl, piperazinyl($C_{1-6}$)alkyl and morpholinyl($C_{1-6}$)alkyl.

Illustrative values of specific substituents on the group $R^{12}$ include methyl, ethyl, n-propyl, benzyl, pyridinylmethyl, chloro, cyano, cyanomethyl, hydroxymethyl, ethoxy, cyclopropylmethoxy, dimethylaminomethyl, aminoethyl, dimethylaminoethyl, dimethylaminocarbonylmethyl, N-methylpiperidinyl, pyrrolidinylethyl, piperazinylethyl and morpholinylmethyl, especially methyl.

Particular values of $R^{12}$ include cyanophenyl, hydroxymethyl-phenyl, pyrazolyl, dimethyl-pyrazolyl, methyl-isoxazolyl, thiazolyl, methyl-thiazolyl, ethyl-thiazolyl, imidazolyl, methyl-imidazolyl, ethyl-imidazolyl, benzyl-imidazolyl, benzimidazolyl, methyl-oxadiazolyl, triazolyl, methyl-triazolyl, propyl-triazolyl, benzyl-triazolyl, pyridinylmethyl-triazolyl, cyanomethyl-triazolyl, dimethylaminomethyl-triazolyl, aminoethyl-triazolyl, dimethylaminoethyl-triazolyl, dimethylaminocarbonyl-methyl-triazolyl, N-methylpiperidinyl-triazolyl, pyrrolidinylethyl-triazolyl, piperazinylethyl-triazolyl, morpholinylethyl-triazolyl, methyl-tetrazolyl, pyridinyl, methyl-pyridinyl, dimethyl-pyridinyl, ethoxy-pyridinyl, cyclopropylmethoxy-pyridinyl, pyridazinyl, chloro-pyridazinyl, pyrimidinyl, pyrazinyl, quinolinyl, isoquinolinyl and quinoxalinyl.

A favoured value of $R^{12}$ is methyl-triazolyl.

A particular subset of the compounds of formula IIA above is represented by the compounds of formula IIB, and pharmaceutically acceptable salts thereof:

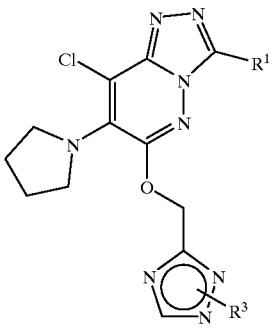

(IIB)

wherein
$R^1$ is as defined with reference to formula I above; and
$R^3$ represents hydrogen or methyl.
In relation to formula IIB above, $R^1$ suitably represents phenyl.
Suitably, $R^3$ represents methyl.

Specific compounds within the scope of the present invention include: 8-chloro-6-(2-methyl-2H-1,2,4-triazol-3-ylmethoxy)-3-phenyl-7-(pyrrolidin-1-yl)-1,2,4-triazolo[4,3-b]pyridazine; 8-chloro-6-(1-methyl-1H-1,2,4-triazol-3-ylmethoxy)-7-(morpholin-4-yl)-3-(thien-2-yl)-1,2,4-triazolo[4,3-b]pyridazine; 8-chloro-6-(1-methyl-1H-1,2,4-triazol-3-ylmethoxy)-3-phenyl-7-(pyrrolidin-1-yl)-1,2,4-triazolo [4,3-b]pyridazine; and salts and prodrugs thereof.

Also provided by the present invention is a method for the treatment and/or prevention of anxiety which comprises administering to a patient in need of such treatment an effective amount of a compound of formula I as defined above or a pharmaceutically acceptable salt thereof or a prodrug thereof.

Further provided by the present invention is a method for the treatment and/or prevention of convulsions (e.g. in a patient suffering from epilepsy or a related disorder) which comprises administering to a patient in need of such treatment an effective amount of a compound of formula I as defined above or a pharmaceutically acceptable salt thereof or a prodrug thereof.

The binding affinity ($K_i$) of the compounds according to the present invention for the α3 subunit of the human $GABA_A$ receptor is conveniently as measured in the assay described hereinbelow. The α3 subunit binding affinity ($K_i$) of the compounds of the invention is ideally 10 nM or less, preferably 2 nM or less, and more preferably 1 nM or less.

The compounds according to the present invention will ideally elicit at least a 40%, preferably at least a 50%, and more preferably at least a 60%, potentiation of the GABA $EC_{20}$ response in stably transfected recombinant cell lines expressing the α3 subunit of the human $GABA_A$ receptor.

Moreover, the compounds of the invention will ideally elicit at most a 30%, preferably at most a 20%, and more preferably at most a 10%, potentiation of the GABA $EC_{20}$ response in stably transfected recombinant cell lines expressing the α1 subunit of the human $GABA_A$ receptor.

The potentiation of the GABA $EC_{20}$ response in stably transfected cell lines expressing the α3 and α1 subunits of the human $GABA_A$ receptor can conveniently be measured by procedures analogous to the protocol described in Wafford et al., *Mol. Pharmacol.*, 1996, 50, 670–678. The procedure will suitably be carried out utilising cultures of stably transfected eukaryotic cells, typically of stably transfected mouse Ltk-fibroblast cells.

The compounds according to the present invention exhibit anxiolytic activity, as may be demonstrated by a positive response in the elevated plus maze and conditioned suppression of drinking tests (cf. Dawson et al., *Psychopharmacology*, 1995, 121, 109–117). Moreover, the compounds of the invention are substantially non-sedating, as may be confirmed by an appropriate result obtained from the response sensitivity (chain-pulling) test (cf. Bayley et al., *J. Psychopharmacol.*, 1996, 10, 206–213).

The compounds according to the present invention may also exhibit anticonvulsant activity. This can be demonstrated by the ability to block pentylenetetrazole-induced seizures in rats and mice, following a protocol analogous to that described by Bristow et al. in *J. Pharmacol. Exp. Ther.*, 1996, 279, 492–501.

In order to elicit their behavioural effects, the compounds of the invention will ideally be brain-penetrant; in other words, these compounds will be capable of crossing the so-called "blood-brain barrier". Preferably, the compounds of the invention will be capable of exerting their beneficial therapeutic action following administration by the oral route.

The invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and favoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

In the treatment of anxiety, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

The compounds in accordance with the present invention may be prepared by a process which comprises reacting a compound of formula III:

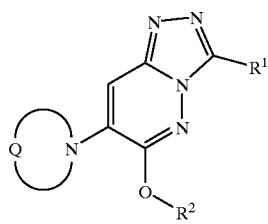

(III)

wherein Q, $R^1$ and $R^2$ are as defined above; with a chlorinating agent.

A suitable chlorinating agent for use in the above reaction is sulphuryl chloride, in which case the reaction can conveniently be brought about by stirring the reactants together in a suitable solvent, e.g. acetic acid, typically at room temperature.

The compounds of formula III above may be prepared by reacting a compound of formula $R^2$—OH with a compound of formula IV:

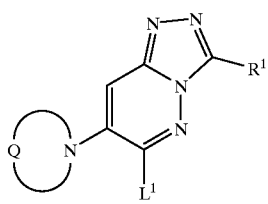

(IV)

wherein Q, $R^1$ and $R^2$ are as defined above; and $L^1$ represents a suitable leaving group.

The leaving group $L^1$ is typically a halogen atom, especially chloro.

The reaction between $R^2$—OH and compound IV is conveniently effected by stirring the reactants in a suitable solvent, typically N,N-dimethylformamide, in the presence of a strong base such as sodium hydride or lithium bis(trimethylsilyl)amide.

The intermediates of formula IV above may be prepared by reacting an aldehyde derivative of formula $R^1$—CHO with a hydrazine derivative of formula V:

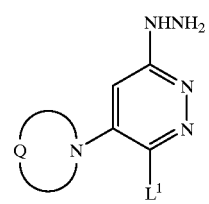

(V)

wherein Q, $R^1$ and $L^1$ are as defined above; followed by cyclization of the intermediate Schiff's base thereby obtained.

The reaction between the aldehyde derivative $R^1$—CHO and compound V is conveniently effected under acidic conditions at an elevated temperature, for example in the presence of a mineral acid such as hydrochloric acid at a temperature in the region of 60° C. Cyclization of the resulting Schiff's base intermediate may then conveniently be carried out by treatment with iron(III) chloride in a suitable solvent, e.g. an alcoholic solvent such as ethanol, at an elevated temperature, typically at the reflux temperature of the solvent; or by treatment with lead(IV) acetate in the presence of acetic acid at an elevated temperature, e.g. a temperature in the region of 60° C.

The intermediates of formula V above may be prepared by reacting the appropriate compound of formula VI:

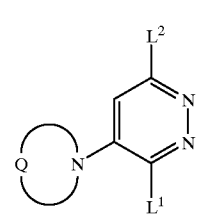

(VI)

wherein Q and $L^1$ are as defined above, and $L^2$ represents a suitable leaving group; with hydrazine hydrate, typically in 1,4-dioxane at the reflux temperature of the solvent; followed, if necessary, by separation of the resulting mixture of isomers by conventional means.

The intermediates of formula IV above may alternatively be prepared by reacting a compound of formula VI as defined above with a substantially equimolar amount of a hydrazine derivative of formula $R^1$—CO—$NHNH_2$ in which $R^1$ is as defined above; followed, if necessary, by separation of the resulting mixture of isomers by conventional means.

The leaving group $L^2$ is typically a halogen atom, especially chloro. In the intermediates of formula VI, the leaving groups $L^1$ and $L^2$ may be the same or different, but are suitably the same, preferably both chloro.

The reaction between the hydrazine derivative $R^1$—CO—$NHNH_2$ and compound VI is conveniently effected by heating the reactants in the presence of a proton source such as triethylamine hydrochloride, typically at reflux in an inert solvent such as xylene or 1,4-dioxane.

The reaction between compound VI and hydrazine hydrate or the hydrazine derivative $R^1$—CO—$NHNH^2$ will, as indicated above, usually give rise to a mixture of isomeric products depending upon whether the hydrazine nitrogen atom displaces the leaving group $L^1$ or $L^2$. Thus, in addition to the required product of formula IV or V, the alternative isomer will usually be obtained to some extent. For this reason it will generally be necessary to separate the resulting mixture of isomers by conventional methods such as chromatography.

In another procedure, the compounds of formula III above may be prepared by reacting a compound of formula VII with a compound of formula VIII:

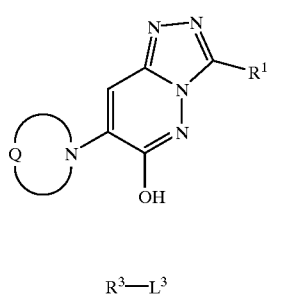

(VII)

$$R^3-L^3$$ (VIII)

wherein Q, $R^1$ and $R^2$ are as defined above; and $L^3$ represents a suitable leaving group.

The leaving group $L^3$ is suitably a halogen atom, typically chloro or bromo.

The reaction between compounds VII and VIII is conveniently effected by stirring the reactants in a suitable solvent, typically N,N-dimethylformamide, in the presence of a strong base such as sodium hydride.

The intermediates of formula VII above may conveniently be prepared by reacting a compound of formula IV as defined above with an alkali metal hydroxide, e.g. sodium hydroxide. The reaction is conveniently effected in an inert solvent such as aqueous 1,4-dioxane, ideally at the reflux temperature of the solvent.

In a further procedure, the compounds of formula III may be prepared by reacting a compound of formula IX with a compound of formula X:

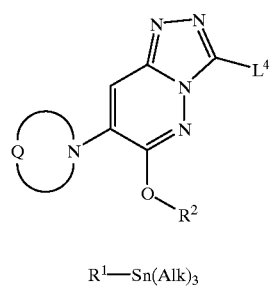

(IX)

$$R^1-Sn(Alk)_3$$ (X)

wherein Q, $R^1$ and $R^2$ are as defined above, Alk represents a $C_{1-6}$ alkyl group, typically n-butyl, and $L^4$ represents a suitable leaving group; in the presence of a transition metal catalyst.

The leaving group $L^4$ is suitably a halogen atom, e.g. bromo.

A suitable transition metal catalyst of use in the reaction between compounds IX and X comprises dichlorobis (triphenylphosphine)-palladium(II).

The reaction between compounds IX and X is conveniently effected in an inert solvent such as N,N-dimethylformamide, typically at an elevated temperature.

The intermediates of formula IX may be prepared by reacting a compound of formula $R^2$—OH with a compound of formula XI:

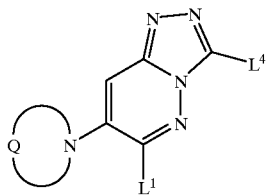

(XI)

wherein Q, $L^1$ and $L^4$ are as defined above; under conditions analogous to those described above for the reaction between $R^2$—OH and compound IV.

Where they are not commercially available, the starting materials of formula VI, VIII, X and XI may be prepared by methods analogous to those described in the accompanying Examples, or by standard methods well known from the art.

It will be understood that any compound of formula I initially obtained from any of the above processes may, where appropriate, subsequently be elaborated into a further compound of formula I by techniques known from the art. For example, a compound of formula I initially obtained wherein $R^2$ is unsubstituted may be converted into a corresponding compound wherein $R^2$ is substituted, typically by standard alkylation procedures, for example by treatment with a haloalkyl derivative in the presence of sodium hydride and N,N-dimethylformamide, or with a hydroxyalkyl derivative in the presence of triphenylphosphine and diethyl azodicarboxylate. Furthermore, a compound of formula I initially obtained wherein $R^2$ represents cyano($C_{1-6}$) alkyl may be converted into the corresponding 3-substituted 1,2,4-triazol-5-yl($C_{1-6}$)alkyl analogue by treatment with the appropriate acyl hydrazine derivative in the presence of a base such as sodium methoxide. Similarly, a compound of formula I initially obtained wherein $R^2$ represents an optionally substituted propargyl moiety may be converted into the corresponding 1,2,3-triazolylmethyl analogue by treatment with azide anion. A compound of formula I initially obtained wherein the $R^2$ substituent is substituted by a halogen atom, e.g. chloro, may be converted into the corresponding compound wherein the $R^2$ substituent is substituted by a di($C_{1-6}$)alkylamino moiety by treatment with the appropriate di($C_{1-6}$)alkylamine, typically with heating in a solvent such as 1,4-dioxane in a sealed tube.

Where the above-described processes for the preparation of the compounds according to the invention give rise to mixtures of stereoisomers, these isomers may be separated by conventional techniques such as preparative chromatography. The novel compounds may be prepared in racemic form, or individual enantiomers may be prepared either by enantiospecific synthesis or by resolution. The novel compounds may, for example, be resolved into their component enantiomers by standard techniques such as preparative HPLC, or the formation of diastereomeric pairs by salt formation with an optically active acid, such as (−)-di-p-toluoyl-d-tartaric acid and/or (+)-di-p-toluoyl-1-tartaric acid, followed by fractional crystallization and regeneration of the free base. The novel compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T.

W. Greene & P. G. M. Wuts, *Protective Groups in Organic Synthesis,* John Wiley & Sons, 1991. The protecting groups may be removed at a convenient subsequent stage using methods known from the art.

The following Examples illustrate the preparation of compounds according to the invention.

The compounds in accordance with this invention potently inhibit the binding of [$^3$H]-flumazenil to the benzodiazepine binding site of human GABA$_A$ receptors containing the α2 or α3 subunit stably expressed in Ltk-cells.

Reagents

Phosphate buffered saline (PBS).

Assay buffer: 10 mM KH$_2$PO$_4$, 100 mM KCl, pH 7.4 at room temperature.

[$^3$H]-Flumazenil (18 nM for α1β3γ2 cells; 18 nM for α2β3γ2 cells; 10 nM for α3β3γ2 cells) in assay buffer.

Flunitrazepam 100 μM in assay buffer.

Cells resuspended in assay buffer (1 tray to 10 ml).

Harvesting Cells

Supernatant is removed from cells. PBS (approximately 20 ml) is added. The cells are scraped and placed in a 50 ml centrifuge tube. The procedure is repeated with a further 10 ml of PBS to ensure that most of the cells are removed. The cells are pelleted by centrifuging for 20 min at 3000 rpm in a benchtop centrifuge, and then frozen if desired. The pellets are resuspended in 10 ml of buffer per tray (25 cm×25 cm) of cells.

Assay

Can be carried out in deep 96-well plates or in tubes. Each tube contains:

300 μl of assay buffer.

50 μl of [$^3$H]-flumazenil (final concentration for α1β3γ2: 1.8 nM; for α2β3γ2: 1.8 nM; for α3β3γ2: 1.0 nM).

50 μl of buffer or solvent carrier (e.g. 10% DMSO) if compounds are dissolved in 10% DMSO (total); test compound or flunitrazepam (to determine non-specific binding), 10 μM final concentration.

100 μl of cells.

Assays are incubated for 1 hour at 40° C., then filtered using either a Tomtec or Brandel cell harvester onto GFIB filters followed by 3×3 ml washes with ice cold assay buffer. Filters are dried and counted by liquid scintillation counting. Expected values for total binding are 3000–4000 dpm for total counts and less than 200 dpm for non-specific binding if using liquid scintillation counting, or 1500–2000 dpm for total counts and less than 200 dpm for non-specific binding if counting with meltilex solid scintillant. Binding parameters are determined by non-linear least squares regression analysis, from which the inhibition constant K$_i$ can be calculated for each test compound.

The compounds of the accompanying Examples were tested in the above assay, and all were found to possess a K$_i$ value for displacement of [$^3$H]-flumazenil from the α2 and/or α3 subunit of the human GABA$_A$ receptor of 100 nM or less.

EXAMPLE 1

8-Chloro-6-(2-methyl-2H-1,2,4-triazol-3-ylmethoxy)-3-phenyl-7-(pyrrolidin-1-yl)-1,2,4-triazolo[4,3-b]pyridazine a) 4-Bromo-1,2-dihydropyridazine-3,6-dione A mixture of bromomaleic anhydride (50 g, 283 mmol) and sodium acetate (76.5 g, 562 mmol) in 40% acetic acid/water (750 ml) was treated with hydrazine monohydrate (16.5 ml, 339 mmol) at room temperature under nitrogen. The brown solution was stirred and heated at 100° C. for 18 hours. Upon cooling the mixture was poured into water (1l) and extracted with ethyl acetate (6×500 ml). The combined extracts were dried (MgSO$_4$), filtered and evaporated to afford the title compound (20 g, 37%) as an orange solid. $^1$H NMR (250 MHz, d$_6$-DMSO) δ7.68 (1H, br s). MS (ES$^+$) m/e 193 [MH]$^+$, 191 [MH]$^+$. This material was used without further purification.

b) 4-Bromo-3,6-dichloropyridazine

A solution of 4-bromo-1,2-dihydropyridazine-3,6-dione (10 g, 52 mmol) in phosphorus oxychloride (100 ml) was stirred and heated at 100° C. under nitrogen for 16 hours. Upon cooling the excess phosphorus oxychloride was removed in vacuo. The residue was azeotroped with toluene (×2), then taken up in dichloromethane/water. The mixture was carefully basified with sodium hydrogen carbonate (solid). It was necessary to dilute the mixture further to get two clear layers. The two layers were separated and the aqueous was extracted with dichloromethane (×3). The combined extracts were dried (Na$_2$SO$_4$), filtered and evaporated. The residue was purified by chromatography on silica gel, eluting with dichloromethane to afford the title compound (5.0 g, 42%) as a colourless solid. $^1$H NMR (250 MHz, CDCl$_3$) δ7.68 (1H, br s). MS (ES$^+$) m/e 230 [MH]$^+$, 228 [MH]$^+$.

c) 3,6-Dichloro-4-(pyrrolidin-1-yl)pyridazine

To a slurry of 4-bromo-3,6-dichloropyridazine (115 g, 0.51 mol) and potassium carbonate (209 g, 1.5 mol) in DMF (1l) was added pyrrolidine (46 ml, 0.56 mol) at 0° C. with stirring. The mixture was allowed to warm to room temperature and then stirred under nitrogen overnight. Water (1.5l) was added and the resultant slurry was filtered. The residue was washed thoroughly with water and diethyl ether, yielding the title compound (110 g, 100%) as a fine white powder. $^1$H NMR (250 MHz, CDCl$_3$) δ2.03 (4H, m), 3.64 (4H, m), 6.46 (1H, s). MS (ES$^+$) m/e 218 [MH]$^+$, 220 [MR]$^+$.

d) 6-Chloro-5-(pyrrolidin-1-yl)-pyridazin-3-ylhydrazine

A solution of 3,6-dichloro-4-(pyrrolidin-1-yl)pyridazine (53 g, 0.24 mol) and hydrazine monohydrate (105 ml, 2.2 mol) in 1,4-dioxane (820 ml) was heated at reflux overnight. The solution was allowed to cool, and dichloromethane was added, precipitating a solid. This was filtered off, affording the title compound as a pale yellow solid (14 g, 27%). The filtrate was concentrated in vacuo, and the residue purified by flash chromatography on silica gel, eluting with 2–5% methanol in dichloromethane containing 0.1% concentrated aqueous ammonia, yielding a further 5 g (4%) of the title compound. $^1$H NMR (250 MHz, CDCl$_3$) δ1.98 (4H, m), 3.26 (2H, br s), 3.57 (4H, m), 6.11 (1H, s), 6.41 (1H, br s). MS (ES$^+$) m/e 214 [MH]$^+$, 216 [MH]$^+$.

e) N-Benzylidene-N'-[6-chloro-5-(pyrrolidin-1-yl) pyridazin-3-yl]hydrazine

To a solution of 6-chloro-5-(pyrrolidin-1-yl)pyridazin-3-ylhydrazine (14 g, 0.063 mol) in 0.1 N hydrochloric acid (600 ml) was added benzaldehyde (6.4 ml, 0.063 mol) dropwise at room temperature. The mixture was stirred at 60° C. for 15 min, yielding a thick slurry. The pH of the solvent was adjusted to ~11 with 4 N aqueous sodium hydroxide solution, and the precipitate filtered off. The residue was washed with water, ethanol and diethyl ether, yielding the title compound as a white solid (14 g, 73%). $^1$H NMR (360 MHz, DMSO) δ1.93 (4H, m), 3.58 (4H, m), 6.57 (1H, s), 7.35 (1H, m), 7.39 (2H, m), 7.66 (2H, d, J=7.1 Hz), 8.06 (1H, s), 11.16 (1H, s). MS (ES$^+$) m/e 302 [MH]$^+$, 304 [MH]$^+$.

f) 6-Chloro-3-phenyl-7-(pyrrolidin-1-yl)-1,2,4-triazolo[4,3-b]pyridazine

A slurry of N-benzylidene-N'-[6-chloro-5-(pyrrolidin-1-yl)pyridazin-3-yl]hydrazine (14 g, 0.046 mol) and lead(IV) acetate (24 g, 0.055 mol) in acetic acid (300 ml) was stirred at 60° C. under nitrogen overnight. The solvent was removed in vacuo, and the residue was purified by flash chromatography on silica gel, eluting with 0–10% methanol in ethyl acetate. The title compound was isolated as a yellow solid (4.1 g, 30%). $^1$H NMR (250 MHz, CDCl$_3$) δ2.05 (4H, m), 3.56 (4H, m), 7.05 (1H, s), 7.51 (3H, m), 8.42 (2H, m). MS (ES$^+$) m/e 300 [MH]$^+$, 302 [MH]$^+$.

g) 6-(2-Methyl-2H-1,2,4-triazol-3-ylmethoxy)-3-phenyl-7-(pyrrolidin-1-yl)-1,2,4-triazolo[4,3-b]pyridazine To (2-methyl-2H-1,2,4-triazol-3-yl)methanol (2.5 g, 0.022 mol; EP-A-421210) in DMF (200 ml) was added a 60% suspension of sodium hydride in mineral oil (1.2 g, 0.031 mol), and the resultant slurry was stirred at room temperature under nitrogen for 1 h. 6-Chloro-3-phenyl-7-(pyrrolidin-1-yl)-1,2,4-triazolo[4,3-b]pyridazine (6.0 g, 0.020 mol) was added, and the mixture was stirred as before for 30 min. Water (600 ml) was added, precipitating a solid. This was filtered off, then washed with water and diethyl ether. The crude product was dissolved in a mixture of ethanol (50 ml) and dichloromethane (110 ml), and then the chlorinated solvent was boiled off. The resultant solution was cooled to 4° C. precipitating the title compound as a white solid (6.3 g, 83%). $^1$H NMR (400 MHz, CDCl$_3$) δ1.97 (4H, m), 3.47 (4H, m), 3.97 (3H, s), 5.59 (2H, s), 6.72 (1H, s), 7.48 (3H, m), 7.95 (1H, s), 8.28 (2H, m); MS (ES$^+$) m/e 377[MH]$^+$.

h) 8-Chloro-6-(2-methyl-2H-1,2,4-triazol-3-ylmethoxy)-3-phenyl-7-(pyrrolidin-1-yl)-1,2,4-triazolo [4,3-b]pyridazine The product from the previous step (25 mg, 0.067 mmol) was dissolved in acetic acid (2 ml) and sulfuryl chloride (16 μl, 0.20 mmol) was added with stirring at room temperature. After 5 min, the solvent was removed in vacuo, and dichloromethane (3 ml) was added to the residue, yielding the title compound as a pale yellow solid, which was recrystallised from ethanol (18 mg, 66%). Data for the title compound: m.p. 174.5–176.0° C. $^1$H NMR (360 MHz, DMSO) δ1.86 (4H, m), 3.76 (4H, m), 3.92 (3H, s), 5.70 (2H, s), 7.61 (3H, m), 8.02 (1H, s), 8.28 (2H, m). MS (ES$^+$) m/e 411 [MH]$^+$, 413 [MH]$^+$.

EXAMPLE 2

8-Chloro-6-(1-methyl-1H-1,2,4-triazol-3-ylmethoxy)-7-(morpholin-4-yl)-3-(thien-2-yl)-1,2,4-triazolo[4,3-b]pyridazine a) 4-(3,6-Dichloropyridazine-4-yl)morpholine This was prepared using the procedure described in Example 1 Step c) except that morpholine was used instead of pyrrolidine. Data for the title compound: $^1$H NMR (250 MHz, CDCl$_3$) δ3.30–3.34 (4H, m), 3.87–3.95 (4H, m), 6.89 (1H, s); MS (ES$^+$) m/e 234, 236, 238 [MH$^+$].

b) 6-Chloro-5-(morpholin-4-yl)pyridazin-3-ylhydrazine

A mixture of 4-(3,6-dichloropyridazin-4-yl)morpholine (5 g, 21.3 mmol) and hydrazine hydrate (7.0 ml, 141 mmol) in 1,4-dioxane (100 ml) was stirred and heated at reflux for 20 hours. Upon cooling the 1,4-dioxane was removed in vacuo. The residue was then partitioned between dichloromethane and saturated aqueous sodium hydrogen carbonate. The aqueous layer was further extracted with dichloromethane (×2). The combined organic extracts were dried (Na$_2$SO$_4$), filtered and evaporated. The residue was purified by chromatography on silica gel, eluting with dichloromethane/methanol/aqueous ammonia (91:8:1) to give 6-chloro-5-(morpholin-4-yl)pyridazin-3-ylhydrazine (3.6 g, 74%): $^1$H NMR (250 MHz, d$_6$-DMSO) δ3.17–3.37 (4H, m), 3.72–3.77 (4H, m), 4.31 (2H, br s), 6.58 (1H, s), 7.97 (1H, br s); MS (ES$^+$) m/e 230, 232 [MH$^+$].

c) 6-Chloro-7-(morpholin-4-yl)-2H-1,2,4-triazolo[4,3-b]pyridazin-3-one

Triphosgene (750 mg, 2.5 mmol) was added to a stirred solution of 6-chloro-5-(morpholin-4-yl)pyridazin-3-ylhydrazine (1.42 g, 6.2 mmol) in 1,2-dichloroethane (60 ml) at room temperature under nitrogen. The mixture was then stirred and heated at reflux for 22 hours. Upon cooling the precipitate was collected by filtration. The solid was washed with diethyl ether and then dried in vacuo to give 6-chloro-7-(morpholin-4-yl)-2H-1,2,4-triazolo[4,3-b]pyridazin-3-one (1.1 g, 67%) which was used without further purification. Data for the title compound: $^1$H NMR (250 MHz, d$_6$-DMSO) δ3.02–3.05 (4H, m), 3.72–3.76 (4H, m), 7.19 (1H, s), 12.57 (1H, br s); MS (ES$^+$) m/e 256, 258 [MH$^+$].

d) 3-Bromo-6-(1-methyl-1H-1,2,4-triazol-3-ylmethoxy)-7-(morpholin-4-yl)-1,2,4-triazolo [4,3-b]pyridazine A mixture of 6-chloro-7-(morpholin-4-yl)-2H-1,2,4-triazolo[4,3-b]pyridazin-3-one (1.1 g, 4.3 mmol) and phosphoryl bromide (25 g) was stirred and heated at 80° C. for 24 hours. Upon cooling the mixture was treated with ice. The aqueous was then basified with aqueous ammonia. The aqueous was then extracted with dichloromethane (×3). The combined extracts were dried (Na$_2$SO$_4$), filtered and evaporated. The residue was purified by chromatography on silica gel, eluting with 5% methanol/dichloromethane to give 3-bromo-6-chloro-7-(morpholin-4-yl)-1,2,4-triazolo[4,3-b]pyridazine (600 mg). $^1$H NMR and mass spectrum revealed the product to a mixture of the desired compound and the 6-bromo compound. This mixture was used without further purification. Sodium hydride (60% dispersion in oil, 80 mg, 2.0 mmol) was added in one portion to a stirred solution of the product from above (600 mg) and (1-methyl-1 H-1,2,4-triazol-3-yl)methanol (240 mg, 2.1 mmol; EP-A-421210) in dry DMF at 0° C. under nitrogen. The ice bath was removed and the mixture was stirred at room temperature for 2 hours. The reaction was quenched with water and then partitioned between ethyl acetate and water. The aqueous layer was further extracted with dichloromethane (×3). The combined organic extracts were dried (Na$_2$SO$_4$), filtered and evaporated. The residue was purified by chromatography on silica gel, eluting with 5 to 8% methanol/dichloromethane to give the title compound (358 mg, 48% for 2 steps). $^1$H NMR (360 MHz, d$_6$-DMSO) δ3.20–3.22 (4H, m), 3.69–3.71 (4H, m), 3.68 (3H, s), 5.47 (2H, s), 7.41 (1H, s), 8.49 (1H, s); MS (ES$^+$) m/e 395, 397 [MH$^+$].

e) 6-(1-Methyl-1H-1,2,4-triazol-3-ylmethoxy)-7-(morphin-4-yl)-3-(thien-2-yl)-1,2,4-triazolo[4,3-b]pyridazine A mixture of 3-bromo-6-(1-methyl-1H-1,2,4-triazol-3-ylmethoxy)-7-(morpholin-4-yl)-1,2,4-triazolo[4,3-b]pyridazine (100 mg, 0.25 mmol) and 2-(tributylstannyl)thiophene (240 ml, 0.75 mmol) in dry DMF (3 ml) was deoxygenated by bubbling through nitrogen gas for 15 minutes. Dichlorobis(triphenylphosphine)palladium(II) (20 mg) was then added. The whole apparatus was further deoxygenated by three "evacuate/ fill N$_2$" cycles. The mixture was then stirred and heated at 100° C. for 16 hours under nitrogen. The reaction mixture was partitioned between dichloromethane and water. The aqueous layer was further extracted with dichloromethane (×2). The combined extracts were dried (Na$_2$SO$_4$), filtered and evaporated. Residual DMF was removed under high vacuum. The residue was purified by chromatography on silica gel, eluting with 5% methanol/dichloromethane to give the title compound (60 mg, 60%). Data for the title compound: $^1$H NMR (360 MHz, CDCl$_3$) δ3.26–3.29 (4H, m), 3.85–3.89 (4H, m), 3.94 (3H, s), 5.64 (2H, s), 7.19–7.23 (2H, m), 7.47–7.59 (1H, m), 8.05 (1H, s), 8.18–8.20 (1H, m); MS (ES$^+$) m/e 399 [MH$^+$].

f) 8-Chloro-6-(1-methyl-1H-1,2,4-triazol-3-methoxy)-7-(morpholin-4-yl)-3-(thien-2-yl)-1,2,4-triazolo[4,3-b]pyridazine This compound was prepared from the product of the previous step using the procedure described in Example 1 Step h). Data for the title compound: m.p.=221.9–222.8° C. $^1$H NMR (360 MHz, CDCl$_3$) δ3.38 (4H, t, J=4.5 Hz), 3.80 (4H, t, J=4.5 Hz), 3.96 (3H, s), 5.59 (2H, s), 7.22 (1H, m) 7.51 (1H, d, J=5.0 Hz), 8.07 (1H, s), 8.19 (1H, d, J=3.7 Hz). MS (ES$^+$) m/e 433 [MH$^+$], 435 [MH$^+$]. Anal. Found C, 47.00; H, 3.64; N, 25.33. $C_{17}H_{17}ClN_7O_2S$. 0.2 H$_2$O requires C, 46.78; H, 4.02; N, 25.67%.

EXAMPLE 3

8-Chloro-6-(1-methyl-1H-1,2,4-triazol-3-ylmethoxy)-3-phenyl-7-(pyrrolidin-1-yl)-1,2,4-triazolo[4,3-b]pyridazine a) 6-(1-Methyl-1H-1,2,4-triazol-3-ylmethoxy)-3-phenyl-7-(pyrrolidin-1-yl)-1,2,4-triazolo [4,3-b]pyridazine This compound was prepared using the procedures described in Example 1 Steps a) to g) but using (1-methyl-1H-1,2,4-triazol-3-yl)methanol (EP-A-421210) instead of (2-methyl-2H-1,2,4-triazol-3-yl)methanol in Step g). $^1$H NMR (360 MHz, CDCl$_3$) δ1.97 (4H, m), 3.55 (4H, m), 3.94 (3H, s), 5.55 (2H, s), 6.68 (1H, s), 7.43 (1H, m), 7.51 (2H, m) 8.06 (1H, s), 8.43 (2H, d, J=7.2 Hz). MS (ES$^+$) m/e 377 [MH$^+$].

b) 8-Chloro-6-(1-methyl-1H-1,2,4-triazol-3-ylmethoxy)-3-phenyl-7-(pyrrolidin-1 -yl)-1,2,4-triazolo [4,3 -b]pyridazine This compound was prepared from the product of the previous step using the procedure described in Example 1 Step h). Data for the title compound: m.p.=198.2–199.1° C. $^1$NMR (360 MHz, CDCl$_3$) δ1.92 (4H, m), 3.73 (4H, m), 3.94 (3H, s), 5.53 (2H, s), 7.48 (3H, m), 8.06 (1H, s), 8.42 (2H, m). MS (ES$^+$) m/e 411 [MH$^+$], 413 [MH$^+$]. Anal. Found C, 55.57; H, 4.30; N, 26.40. $C_{19}H_{19}ClN_8O$ requires C, 55.54; H, 4.66; N, 27.27%.

What is claimed is:

1. A compound of formula I, or a salt thereof:

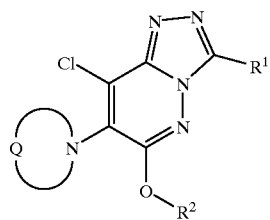

(I)

wherein the ring formed by Q together with the N to which Q is attached represents azetidine, pyrrolidine, piperidine, morpholine or thiomorpholine ring, optionally substituted C$_{1-6}$ alkyl, R$^1$ represents C$_{3-7}$cycloalkyl, phenyl, furyl, thienyl or pyridinyl, any of which groups may be optionally substituted with one or two substituents, each substituent independently is C$_{1-6}$alkyl, aryl(C$_{1-6}$)alkyl, pyridyl (C$_{1-6}$)alkyl, halogen, halo(C$_{1-6}$)alkyl, cyano, cyano(C$_{1-6}$)alkyl, hydroxy, hydroxymethyl, C$_{1-6}$alkoxy, C$_{3-7}$cycloalkyl(C$_{1-6}$)alkoxy, C$_{3-7}$cycloalkoxy, amino (C$_{1-6}$)alkyl, di(C$_{1-6}$)alkylamino(C$_{1-6}$)alkyl, di(C$_{1-6}$)alkylaminocarbonyl(C$_{1-6}$)alkyl, N-(C$_{1-6}$)alkylpiperidinyl, pyrrolidinyl(C$_{1-6}$)alkyl, piperazinyl (C$_{1-6}$)alkyl, morpholinyl(C$_{1-6}$)alkyl, di(C$_{1-6}$)alkylmorpholinyl(C$_{1-6}$)alkyl or imidazolyl(C$_{1-6}$)alkyl; and R$^2$ represents cyano(C$_{1-6}$)alkyl, hydroxy(C$_{1-6}$)alkyl, C$_{3-7}$cycloalkyl(C$_{1-6}$) alkyl, propargyl, azetidinylcarbonyl(C$_{1-6}$)alkyl, pyrrolidinylcarbonyl (C$_{1-6}$)alkyl, piperidinylcarbonyl(C$_{1-6}$)alkyl, piperazinylcarbonyl(C$_{1-6}$)alkyl, morpholinylcarbonyl (C$_{1-6}$)alkyl, thiomorpholinylcarbonyl(C$_{1-6}$)alkyl, aryl (C$_{1-6}$)alkyl, pyridinyl(C$_{1-6}$)alkyl, quinolinyl(C$_{1-6}$)alkyl, isoquinolinyl(C$_{1-6}$)alkyl, pyridazinyl(C$_{1-6}$)alkyl, pyrimidinyl(C$_{1-6}$) alkyl, pyrazinyl(C$_{1-6}$)alkyl, quinoxalinyl(C$_{1-6}$)alkyl, furyl(C$_{1-6}$)alkyl, benzofuryl (C$_{1-6}$)alkyl, dibenzofuryl(C$_{1-6}$)alkyl, thienyl(C$_{1-6}$)alkyl, benzthienyl(C$_{1-6}$)alkyl, pyrrolyl(C$_{1-6}$)alkyl, indolyl(C$_{1-6}$)alkyl, pyrazolyl(C$_{1-6}$)alkyl, indazolyl(C$_{1-6}$)alkyl, oxazolyl(C$_{1-6}$)alkyl, isoxazolyl(C$_{1-6}$)alkyl, thiazolyl(C$_{1-6}$)alkyl, isothiazolyl(C$_{1-6}$)alkyl, imidazolyl(C$_{1-6}$)alkyl, benzimidazolyl(C$_{1-6}$)alkyl, oxadiazolyl(C$_{1-6}$)alkyl, thiadiazolyl(C$_{1-6}$)alkyl, triazolyl(C$_{1-6}$)alkyl, or tetrazolyl(C$_{1-6}$)alkyl, any of which groups may be optionally substituted with one or two substituents, each substituent independently is C$_{1-6}$alkyl, aryl(C$_{1-6}$)alkyl, pyridyl(C$_{1-6}$)alkyl, halogen, halo(C$_{1-6}$)alkyl, cyano, cyano(C$_{1-6}$)alkyl, hydroxy, hydroxymethyl, C$_{1-6}$)alkoxy, C$_{3-7}$cycloalkyl(C$_{1-6}$) alkoxy, C$_{3-7}$cycloalkoxy, amino(C$_{1-6}$)alkyl, di(C$_{1-6}$)alkylamino(C$_{1-6}$)alkyl, di(C$_{1-6}$)alkylaminocarbonyl (C$_{1-6}$)alkyl, N-(C$_{1-6}$)alkylpiperidinyl, pyrrolidinyl(C$_{1-6}$)alkyl, piperazinyl(C$_{1-6}$)alkyl, morpholinyl(C$_{1-6}$) alkyl, di(C$_{1-6}$)alkylmorpholinyl(C$_{1-6}$)alkyl or imidazolyl(C$_{1-6}$)alkyl.

2. A compound as claimed in claim 1 represented by formula IIA, or salts thereof:

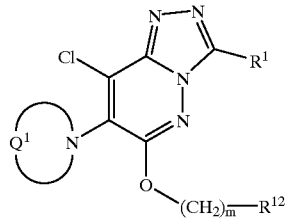

(IIA)

wherein

R$^1$ is as defined in claim 1;

m is 1 or 2;

the ring formed by Q$^1$ together with the N to which Q$^1$ is attached represents a pyrrolidine or morpholine ring; and R$^{12}$ represents aryl or heteroaryl, either of which groups may be optionally substituted with one or two substituents, each substituent independently is C$_{1-6}$alkyl, aryl(C$_{1-6}$)alkyl, pyridyl(C$_{1-6}$)alkyl, halogen, cyano, cyano(C$_{1-6}$)alkyl, hydroxymethyl, C$_{1-6}$alkoxy, C$_{3-7}$cycloalkyl(C$_{1-6}$)alkoxy, di(C$_{1-6}$)alkylamino(C$_{1-6}$) alkyl, amino(C$_{1-6}$)alkyl, di(C$_{1-6}$)alkylaminocarbonyl ($C_{1-6}$)alkyl, N-($C_{1-6}$)alkylpiperidinyl, pyrrolidinyl($C_{1-6}$)alkyl, piperazinyl($C_{1-6}$)alkyl, morpholinyl($C_{1-6}$)alkyl.

3. A compound as claimed in claim 2 represented by formula IIB, and pharmaceutically acceptable salts thereof:

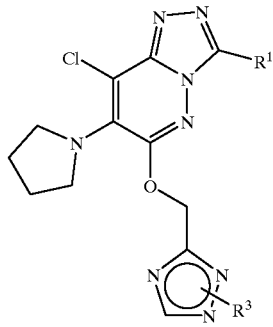

(IIB)

wherein
$R^1$ is as defined in claim 1; and
$R^3$ represents hydrogen or methyl.

4. A compound selected from:
8-chloro-6-(2-methyl-2H-1,2,4-triazol-3-ylmethoxy)-3-phenyl-7-(pyrrolidin-1-yl)-1,2,4-triazolo[4,3-b]pyridazine;
8-chloro-6-(1-methyl-1H-1,2,4-triazol-3-ylmethoxy)-7-(morpholin-4-yl)-3-(thien-2-yl)-1,2,4-triazolo[4,3-b]pyridazine;
8-chloro-6-(1-methyl-2H-1,2,4-triazol-3-ylmethoxy)-3-phenyl-7-(pyrrolidin-1-yl)-1,2,4-triazolo[4,3-b]pyridazine; or
salts thereof.

5. A pharmaceutical composition comprising a compound of formula I as defined in claim 1 or a pharmaceutically acceptable salt thereof in association with a pharmaceutically acceptable carrier.

6. A process for the preparation of a compound as claimed in claim 1, which comprises reacting a compound of formula III:

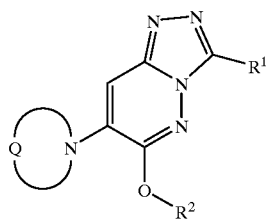

(III)

wherein Q, R1 and R2 are as defined in claim 1; with a chlorinating agent.

7. A method for the treatment and/or prevention of anxiety which comprises administering to a patient in need of such treatment an effective amount of a compound of formula I as defined in claim 1, or a pharmaceutically acceptable salt thereof.

8. A method for the treatment and/or prevention of convulsions which comprises administering to a patient in need of such treatment an effective amount of a compound of formula I as defined in claim 1, or a pharmaceutically acceptable salt thereof.

* * * * *